US011901052B2

United States Patent
Willis et al.

(10) Patent No.: US 11,901,052 B2
(45) Date of Patent: Feb. 13, 2024

(54) SYSTEM AND METHOD FOR HANDLING EXCEPTIONS DURING HEALTHCARE RECORD PROCESSING

(71) Applicant: Moxe Health Corporation, Madison, WI (US)

(72) Inventors: Tomas C. Willis, Madison, WI (US); Daniel P. Wilson, Madison, WI (US)

(73) Assignee: Moxe Health Corporation, Madison, WI (US)

( * ) Notice: Subject to any disclaimer, the term of this patent is extended or adjusted under 35 U.S.C. 154(b) by 0 days.

(21) Appl. No.: 18/111,798

(22) Filed: Feb. 20, 2023

(65) Prior Publication Data
US 2023/0207080 A1 Jun. 29, 2023

Related U.S. Application Data

(63) Continuation of application No. 16/697,178, filed on Nov. 26, 2019, now Pat. No. 11,587,652.

(51) Int. Cl.
*G16H 10/60* (2018.01)
*G06F 21/64* (2013.01)
*G06F 21/56* (2013.01)
*G06F 11/10* (2006.01)

(52) U.S. Cl.
CPC ......... *G16H 10/60* (2018.01); *G06F 11/1024* (2013.01); *G06F 21/565* (2013.01); *G06F 21/64* (2013.01)

(58) Field of Classification Search
USPC .......................................................... 705/3
See application file for complete search history.

(56) References Cited

U.S. PATENT DOCUMENTS

| | | | | |
|---|---|---|---|---|
| 2013/0006416 A1* | 1/2013 | Canter | ............... | G06Q 30/0241 700/236 |
| 2013/0179586 A1* | 7/2013 | Branson | ................. | G06F 16/00 709/231 |
| 2013/0297344 A1* | 11/2013 | Cosentino | .......... | A61N 1/37211 705/3 |
| 2015/0348076 A1* | 12/2015 | Mondragon | .......... | G06F 16/215 705/7.34 |
| 2017/0372029 A1* | 12/2017 | Saliman | ................. | G16H 10/60 |
| 2019/0034592 A1* | 1/2019 | Gupta | .................... | G16H 50/20 |

(Continued)

*Primary Examiner* — Sakinah White Taylor
(74) *Attorney, Agent, or Firm* — Foley & Lardner LLP

(57) ABSTRACT

Methods, systems, and apparatuses to improve the handling of exceptions during the retrieval and processing of health records from various data sources are provided. During the retrieval and processing of health records, exceptions to typical behavior are recorded with context at the data extraction protocol level, at the health record level and at the level of elements with the document. Accordingly, insights may be developed and configurations, rules, or coding changes, based on the detected exceptions may be proposed. In some instances, an operator may be notified about the exceptions such that the operator may act on the insight. In some instances, the processing of extracted records (documents, messages) may be deferred until the operator has made appropriate changes to configuration, rules, or code. In some instances, the system may supplement and/or replace the operator with machine learning engines that act on the developed insights.

20 Claims, 12 Drawing Sheets

(56) References Cited

U.S. PATENT DOCUMENTS

| | | | |
|---|---|---|---|
| 2020/0272998 A1* | 8/2020 | Jameson | G06F 16/335 |
| 2021/0081407 A1* | 3/2021 | Kidd | G06Q 10/20 |
| 2021/0090694 A1* | 3/2021 | Colley | G16H 15/00 |

* cited by examiner

Fig. 2

Panel 204:

| General | Doctors | Medication | History | Insurance |

Patient Information

Name: Last, First
Address: 123 Anywhere,
Anytown, Anycity, USA

Height: 6'-1"
Weight: 190 lbs
Blood Type: A+

Allergies

Contact Information

Name:
Address:

Phone:

Panel 208:

| General | Doctors | Medication | History | Insurance |

Patient Name/Identifier
08/30/02 11:00 AM
EMERGENCY DEPARTMENT / Dr. Scarlet, Bates No. 1

Patient admitted to the ER at City Hospital with expressive aphasia & right facial droop. In no acute distress.

Chief complaint: slurred speech & difficulty finding words.

[Temp 36 F  P 62  R 18  BP 180/75  Allergies: none known] — 212

Past history: HTN (hypertension), treated with Lopressor  Coronary artery disease (CAD), treated with Lipitor for high cholesterol & Ecotrin daily. Abdominal hysterectomy Physical exam: all within normal limits except the right facial droop with aphasia.

IV is started EKG is done (unremarkable) Blood sugar is checked (ok)

Neurology is called.

CT scan of the brain is done. Labs are drawn including hematology & chemistry — 220

Transfer under the care of Dr. Fellows.

216

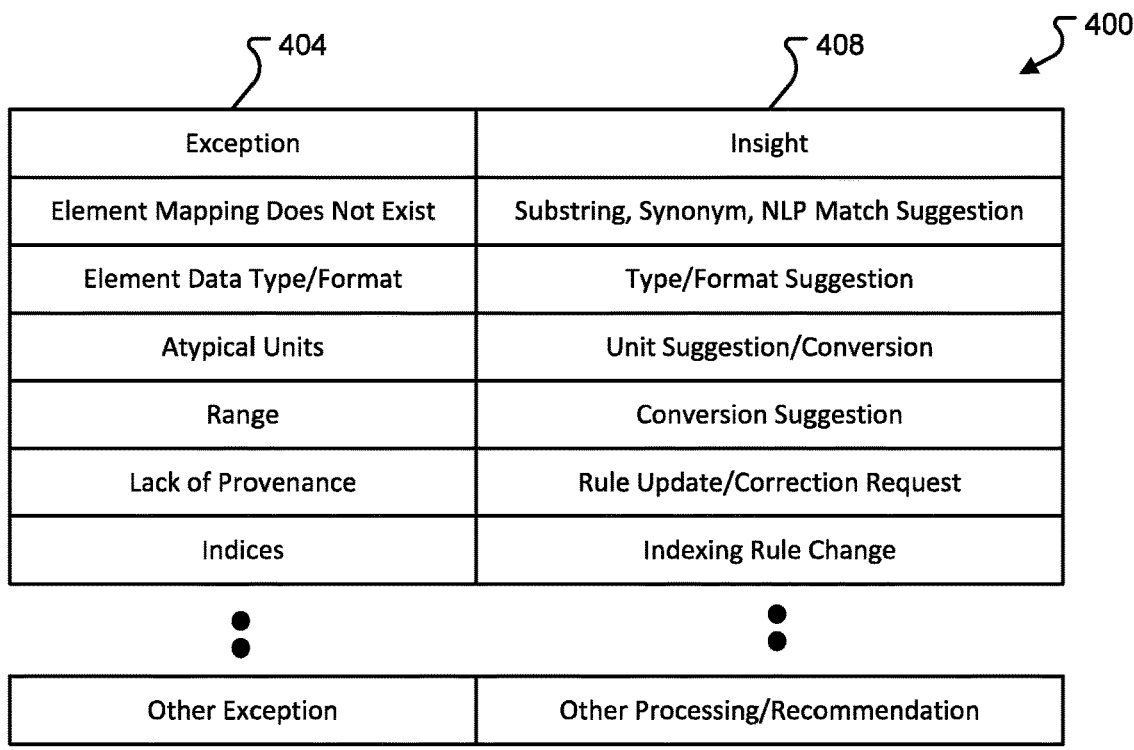
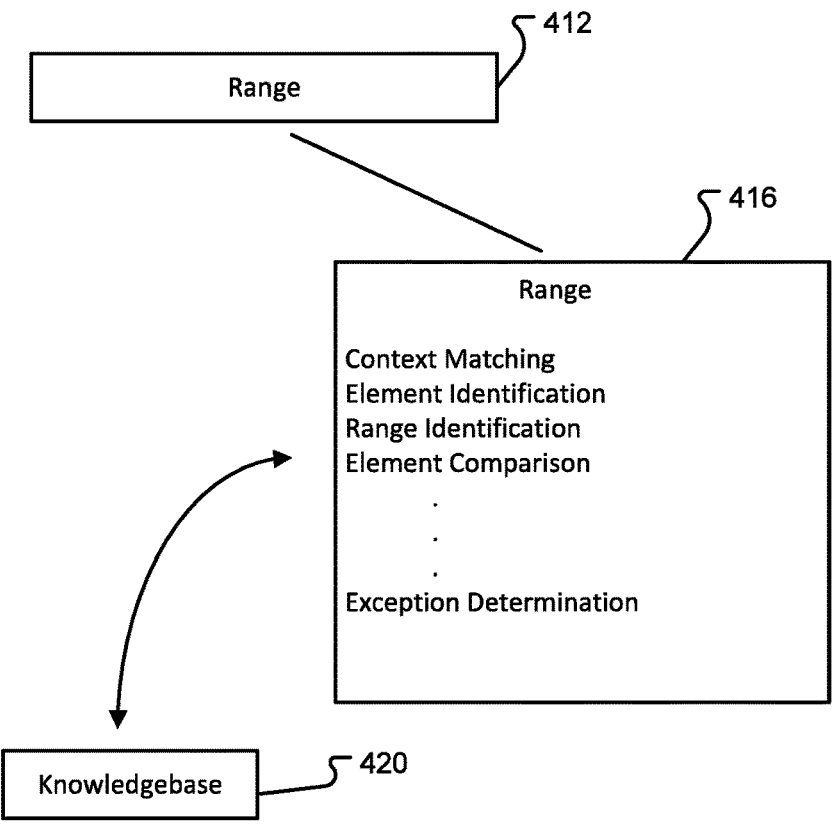
Fig. 4

| General | Doctors | Medication | History | Insurance |

Patient Name/Identifier
08/30/02 11:00 AM
EMERGENCY DEPARTMENT / Dr. Scarlet, Bates No. 1

Patient admitted to the ER at City Hospital with expressive aphasia & right facial droop. In no acute distress.

Chief [Convert to 96.8] & difficulty finding words.

Temp [Exception Details]
[Do Not Convert] Allergies: none known

Past history: HTN (hypertension), treated with Lopressor Coronary artery disease (CAD), treated with Lipitor for high cholesterol & Ecotrin daily. Abdominal hysterectomy Physical exam: all within normal limits except the right facial droop with aphasia.

IV is started EKG is done (unremarkable) Blood sugar is checked (ok)

Neurology is called.

CT scan of the brain is done. Labs are drawn including hematology & chemistry

Transfer under the care of Dr. Fellows.

*Fig. 8*

| Exception ID (904) | Exception Details (908) | Action Taken (912) |
|---|---|---|
| 12A7F | 01 | Accepted |
| 18FGA | 01/02 | Accept/Code Change |
| ⋮ | ⋮ | ⋮ |
| 48FFE | 03 | None |

*Fig. 9*

SYSTEM AND METHOD FOR HANDLING EXCEPTIONS DURING HEALTHCARE RECORD PROCESSING

BACKGROUND

Health records are contained in a variety of source systems at healthcare organizations, such as, but not limited to, electronic medical records system (EMR), electronic health records system (EHR), medical billing systems, laboratory information system (LIS), hospital document management systems, health plan claims databases, content management systems (CMS), document management systems (DMS), genomics data sets, radiology imaging systems (RIS), and healthcare vendor-neutral databases (VNA), generally referred to as healthcare information technology (HIT) systems. While HIT systems allow operators to customize document properties, types, code sets, etc., the data and communications standards may be implemented slightly differently at each of the HIT systems. Further, within each HIT system, healthcare records are stored in a wide variety of formats and accessed through a variety of protocols. While interoperability solutions exist that extract healthcare information from source systems to support interchange with external systems, when extracting documents or processing messages from an EMR/EHR or other HIT system, encountering an exception to typical behaviors and properties when retrieving a record, or encountering an exception in the elements or format of the retrieved record, may prevent the operation of extracting the whole document or message with the highest precision. For example, an existing interoperability solution may do a poor job of normalizing an extracted record by skipping over elements with abnormal data formats or character set encoding, or otherwise skipping over elements and/or data not meeting, matching, or adhering to one or more preset data formats.

SUMMARY

In accordance with examples of the present disclosure, a method, system, and apparatus to improve the handling of exceptions during the retrieval and processing of health records from various data sources is provided. The data sources may exist at a broad range of healthcare organizations, including a health system, Health Information Exchange (HIE), lab, digital health company, nursing home, pharmacy, governmental agency, health plan/insurer or individual custodian of the health care data of an individual (themselves or a family member, for example). The healthcare documents may be expected to contain various types of medical records, containing different types of data (text, numbers, images, audio recordings, video recordings, genomics data, spreadsheets, . . . ), in discrete, non-discrete, structured or unstructured formats, across the gamut of health and personal data, including, but not limited to clinical records, demographic data, claims data, pharmacy data, genomic data, dental data, and social determinants. Processing includes but is not limited to retrieval, manipulation, normalization, indexing, ingestion, scoring, routing, tagging, and formatting, as well as using records for training, tuning and testing machine learning.

During the retrieval and processing of health records, exceptions to typical behaviors are recorded with context at the data extraction protocol level, at the health record level, and at the level of elements with the document. The system may develop insights, such as proposed configuration, rule or coding changes, based on the detected exceptions. The system may notify the operator about the exceptions and provide an opportunity to act on the insights, such as implement configuration changes or specify the code set of an element in the record. The system may provide a method to defer processing of extracted records (documents, messages) until the operator has made appropriate changes to configuration, rules or code and a means to reprocess the records when ameliorative changes are in place. The system may supplement and/or replace the operator with machine learning engines that act on these insights.

In some examples, the context of a record within a set of records or that of an element within a record may change what is an exception: for example, if the documentation describing a radiology lab visit does not include copies of the images described in the text record of this encounter, for example, this may constitute an exception to expected or acceptable documentation. In another example, when a system is processing a health document using an automated process to index, tag, categorize, score, etc., a document using a set of analysis rules, a scoring rubric, or a machine learning process like Natural Language Processing (NLP), a criterion for successful processing may include the extraction of a certain set of mandatory elements, tags, categories, discrete values, inferred states, etc. If the required set of data items cannot be generated by the automated process, then an exception condition exists, and the disclosed system processes the document following the methods herein described.

In another example, if a user of a health records IT system was presented with an medically-relevant actionable insight (an opportunity to make a healthcare decision or take an action based on some information presented to them) and the health records IT system records that their decision was not the result expected by the external system providing these medical insights, then the differences in a decision may be an exception to expected behavior as described in this teaching. Note that this example of a medical insight system whose results are stored in the health records system is unrelated to and distinct from the exceptions disclosed below.

In accordance with at least one example of the present disclosure, if a record is requested and the process is unable to obtain the complete record and any associated records referenced recursively in the first document, that is an exception. In accordance with at least one example of the present disclosure, if an external system or process (i.e. claim processing clearinghouse, clinical decision support tool, eligibility system, etc.) determines that a process cannot complete due to insufficient information, and that information can be gathered via one or more services, the process failure in the external system may be monitored by one or more exception handling services and treated the same or similar way as other exceptions, where automatic and/or manual intervention may be used to provide missing information that would allow the original external system or process to be adjudicated/completed.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIG. 2 illustrates depicts details of an electronic health record in accordance with examples of the present disclosure;

FIG. 4 depicts example exceptions and insights in accordance with examples of the present disclosure;

FIG. 8 depicts an example insight suggestion provided at a graphical user interface in accordance with examples of the present disclosure;

FIG. 9 depicts details of a data structure in accordance with examples of the present disclosure;

DETAILED DESCRIPTION

Figure 1:
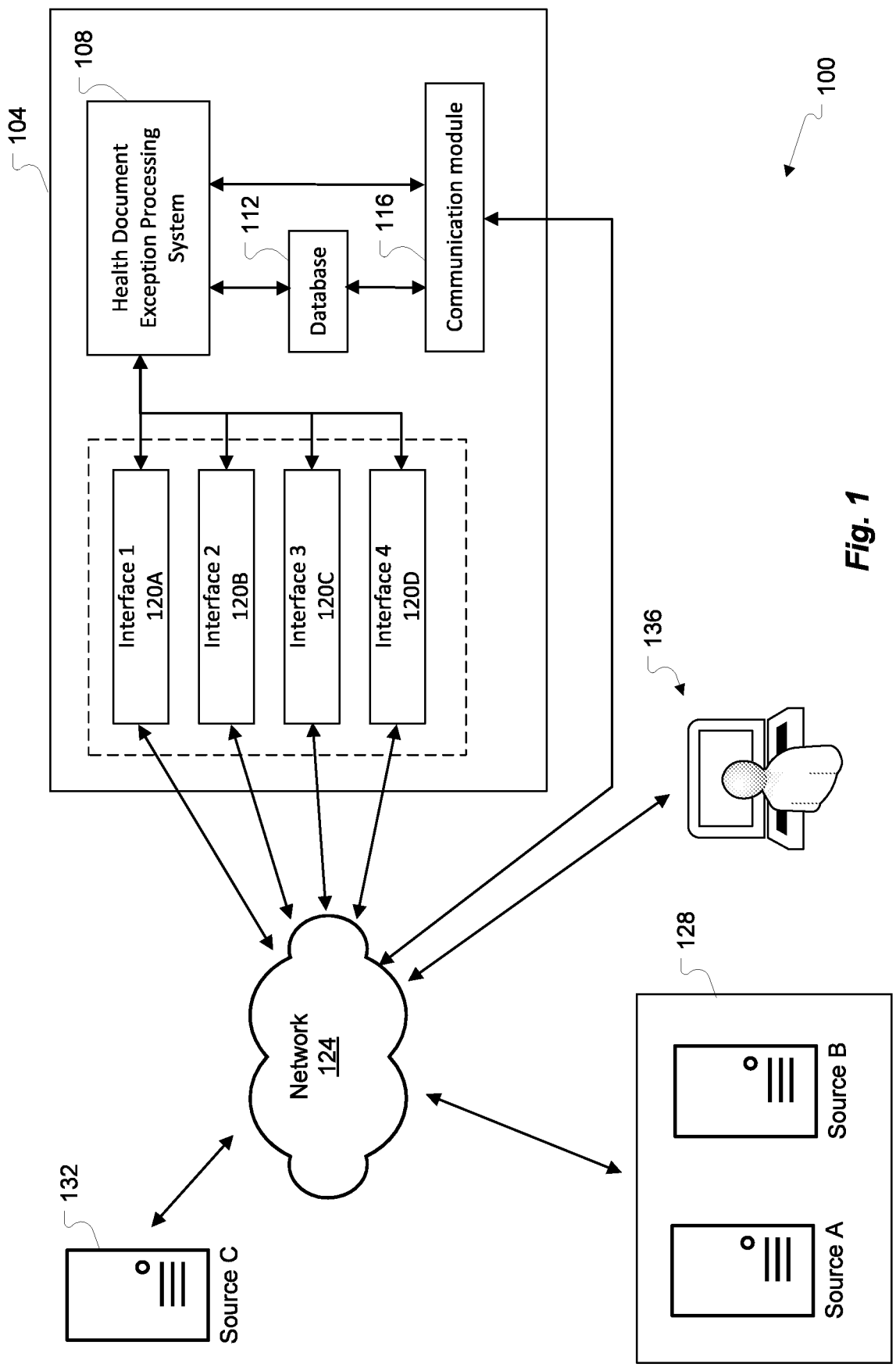
FIG. 1 illustrates a first block diagram directed to a health document processing system in accordance with the aspects a of the disclosure.

The ensuing description provides embodiments only and is not intended to limit the scope, applicability, or configuration of the claims. Rather, the ensuing description will provide those skilled in the art with an enabling description for implementing the embodiments. It being understood that various changes may be made in the function and arrangement of elements without departing from the spirit and scope of the appended claims.

In accordance with examples of the present disclosure, a system and method for improving the handling of exceptions during the retrieval and manipulation of health records from various data sources is provided. Healthcare records include a variety of documents stored in physical media and electronic media. These records exist in health records systems maintained by Health Care Organizations ("HCO") (health plans, health systems, providers, employers, medical labs, pharmacies, nursing homes, long-term care facilities, digital health companies, medical device manufacturers, individual patients and families, pharmaceutical and medical test laboratories, etc.) An electronic health record may include, but is not limited to, clinical notes entered into an electronic medical records (EMR) system, medical billing information, lab results, radiology images and reports, prescription records, family medical history, hospital admissions and discharge records, discrete measurements like heart rate, digitized physical medical records and treatment plans. These medical records may belong to a health system and be stored in one or more health information technology (HIT) source systems, such as EMRs, laboratory information systems (LIS), content management systems (CMS), picture archive and communication system (PACS) or other health system HIT system. The records may alternatively be accessible via one or more health information exchange (HIE) sources or otherwise stored in a storage area and accessible via one or more information technology systems of a health plan or a system of another steward of healthcare records.

There are a variety of processes that require data from health records to be extracted from their current source location. These include identification of potential participants in pharmaceutical research projects, population health studies, authorization of services, support of billing queries, institutional qualities measures, external auditing and gap closure. Records can be extracted from each source system for electronic health records by one or more communication or reporting protocols, such as but not limited to HL7 version 2, X12, Fast Healthcare Interoperability Resources (FHIR), XCA, SQL database queries, and/or other bespoke reporting solutions. The health records may be organized as messages in a data stream, previously created records in a document storage system, or documents created at the time of request, for example. The health records data may be extracted in a variety of formats, based on the nature, configuration and capacities of the source system, including, but not limited to CDR, CDA, C-CDA, FHIR, comma-separated value files and proprietary binary, or other, formats, as well as formats not yet devised. Data elements within a record may be discrete data of a certain type, generally containing specific units, such as body temperature in degrees Celsius. In some instances, the health record may include non-discrete data, such as but not limited to physician's visit notes. A health record may contain one or more data elements. Each record and element may have a name or description, a type of content, the content or value itself, a data format, a data encoding, a character code set, a medical code set and other metadata. A document may have required data elements and/or optional data elements, with optional or required format. The presence or absence of some data element(s) may imply the presence or absence of some other data element(s).

Existing solutions for processing (including extracting, normalizing and other processes mentioned earlier in this disclosure) health records from data sources work well when the properties and characteristics of the records being extracted are well-known before the record is extracted. In addition to complexities of the data extraction protocols, record types and record element varieties, many healthcare IT solutions permit operators to customize the record names, content, element types and metadata. In addition, different HIT vendors will support industry standards for protocols and records with some variations. This situation in the healthcare IT industry creates opportunities for exceptions to occur when existing solutions extract, process, and/or normalize healthcare records.

FIG. 1 depicts a medical records network 100 in accordance with examples of the present disclosure. The medical records network 100 may include a health document processing system 104, one or more sources of medical records 128 and 132, and one or more targets 136, also referred to as a requester. The target 136 may request, either explicitly or as part of another process, that a health record be subjected to one or more processing operations. For example, the target 136 may request a specific health record for specific look-up or the target may request a batch of health records for normalization, analysis, and distribution. The health document processing system 104 may include a health document exception processing system 108, one or more databases 112, one or more communication modules 116, and one or more user interfaces 120A-120D. In some examples, the health document processing system 104 may be a portal that provides functionalities for a point of access on the web or Internet. That is, as will be described below, the health document processing system 104 may provide centralized management capabilities for receiving a request for a medical record and fulfilling such request by retrieving medical record information from one or more sources, such as source 128, assembling a medical record, and providing the assembled medical record to one or more targets, such as target 136. Accordingly, the one or more targets 136 may interact with one or more of the user interfaces 120A-120D to provide a medical record request to the health document processing system 104 and receive the requested medical records from the health document processing system 104 via the one or more user interfaces 120A-120D.

As previously discussed, the health document processing system 104 may be a portal. Accordingly, a management entity may manage access by the target, or requester 136. Moreover, one or more rules limiting the access of the requester and/or establishing eligibilities with respect to what type of medical record information may be viewed by the requester. Moreover, the management entity may include a number of tools to configure, set up, and operate the portal. For example, the management entity may include a number of portlets customized for various users. It may include specialized processing subsystems to process and generate one or more of the user interfaces 120A-D.

The health document processing system 104 may store one or more medical records in the database 112. More specifically, the database 112 may store information associated with medical records gathered from the one or more sources 128 and/or 132, and may act as a repository of medical record information. Moreover, as one or more medical records are assembled from information gathered from the one or more sources 128 and/or 132, the health document processing system 104 may process each of the one or more medical records to determine if an exception exists. In some instances, the one or more medical records are already assembled and the health document processing system 104 acts on the information, or data, contained in the medical record to determine if an exception is present. Thus, for example, the health document exception processing system 108 may process information associated with a medical record as a medical record is being assembled or may process information from a medical record that is already assembled.

Each of the health document processing system 104, the one or more sources of medical records 128 and/or 132, and/or the one or more targets 136 may communicate or otherwise be communicatively coupled to one another via the network 124. The network 124 may be without limitation, a Wide Area Network (WAN), such as the Internet, a Local Area Network (LAN), a Personal Area Network (PAN), a Public Switched Telephone Network (PSTN), a Plain Old Telephone Service (POTS) network, a cellular communications network, or combinations thereof. The Internet is an example of the communication network that constitutes an Internet Protocol (IP) network including many computers, computing networks, and other communication devices located all over the world, which are connected through many systems and other means. In one configuration, the telecommunication network is a public network supporting the TCP/IP suite of protocols. Communications supported by the telecommunication network include real-time, near-real-time, and non-real-time communications.

FIG. 2 depicts a medical record 204 in accordance with examples of the present disclosure. The medical record 204 may be a medical record retrieved from one or more sources as previously discussed. In addition, the medical record 204 depicted in FIG. 2 should not be considered limiting; that is, the medical record 204 is an example medical record; other medical records, including varying types of medical records (e.g., electronic, paper, or otherwise) are contemplated herein. Moreover, as medical record 204 is an example of a medical record, the actual medical records retrieved from one or more sources may be different than that which is displayed in FIG. 2.

In addition, the medical record 204 may include various organizations or partitions separating medical record information. For example, a medical record 204 may include a general portion which provides general information about a patient; a doctors portion which provides information about and/or to doctors associated with the patient; a medication portion which provides additional information about medications that have been and/or are prescribed to the patient; a history portion providing information about past treatments and/or care; and an insurance portion which may provide additional insurance information and/or billing related information. As the previously described portions are provide for example purposes only, a medical record may include more or fewer portions than that which has been described above. The medical record 204 may include a patient name and/or identifier, such as a reference number; the patient name and/or identifier may be utilized by the health document processing system 104 to associate medical record information with a specific or specified patient or individual.

As further depicted in FIG. 2, the medical record portion 208 generally depicts an example history portion of the medical record 204. As previously described, the health document processing system 104 may analyze one or more portions of the medical record, such as medical record portion 208, and determine if data, or information, associated with a label is within an expected ranged. For example, the health document exception processing system 108 may analyze each piece of information, or data or values associated with one or more elements, contained in the medical record to determine if a discrepancy exists. As one example, the temperature element 212 associated with the medical record 204 indicates that a temperature of the patient was recorded as being "36 F", which is usually understood to be thirty-six degrees Fahrenheit and the record indicates the patient is alive. The health document exception processing system 108 may identify that an exception exists and therefore flag or mark the identified exception for further processing. Returning to the previous example, upper and lower limits may be associated with numerical type data elements such as a temperature. If the numerical type data element is above an upper limit or below a lower limit, the numerical type data may be flagged or otherwise marked. Of course, data elements may include one or more acceptable ranges, or otherwise be associated with one or more acceptable templates. As another example, the temperature element 212 may indicate a temperature expressed as text, for example, "thirty-six F". Accordingly, the health document exception processing system 108 may not flag or may not mark the temperature portion of the medical record 204 if the text indicates that the temperature is between the upper and lower limits.

Alternatively, the health document exception processing system 108 may flag or mark the temperature portion of the medical record 204 and provide a suggestion for bringing the flagged, or marked, portion of the record into compliance or otherwise with one or more templates or data field requirement. That is, the health document exception processing system 108 may provide a suggestion indicating that the temperature element 212 may be converted to different units. In some instances a graphical user interface may be presented to a user asking the user to accept, reject, or propose a different value or comment. In some instances, the health document exception processing system 108 may automatically bring the flagged, or marked, portion of the record into compliance or otherwise with one or more templates or data field requirement, track and store the conversion, and present a list of converted elements to a user as part of a record input and/or processing process. Moreover, the health document exception processing system 108 may revert back to the original value if a user or other process indicates that the original value may be a desired value.

As another example, the medical record 204 may include status and/or notes, such as status and/or notes 216/220. As part of the record processing process, an exception process may determine whether or not images and/or lab results are included with the medical record 204 or otherwise accessible. For example, a note may be processed with one or more natural language processing systems such that the health document exception processing system 108 may determine whether or addition information, data, or other items are and/or should be associated with medical record 204. As previously discussed, if such additional items are not provided from the source 128 for example, the health document exception processing system 108 may raise an exception and/or provide a notification to a user.

Figure 3:
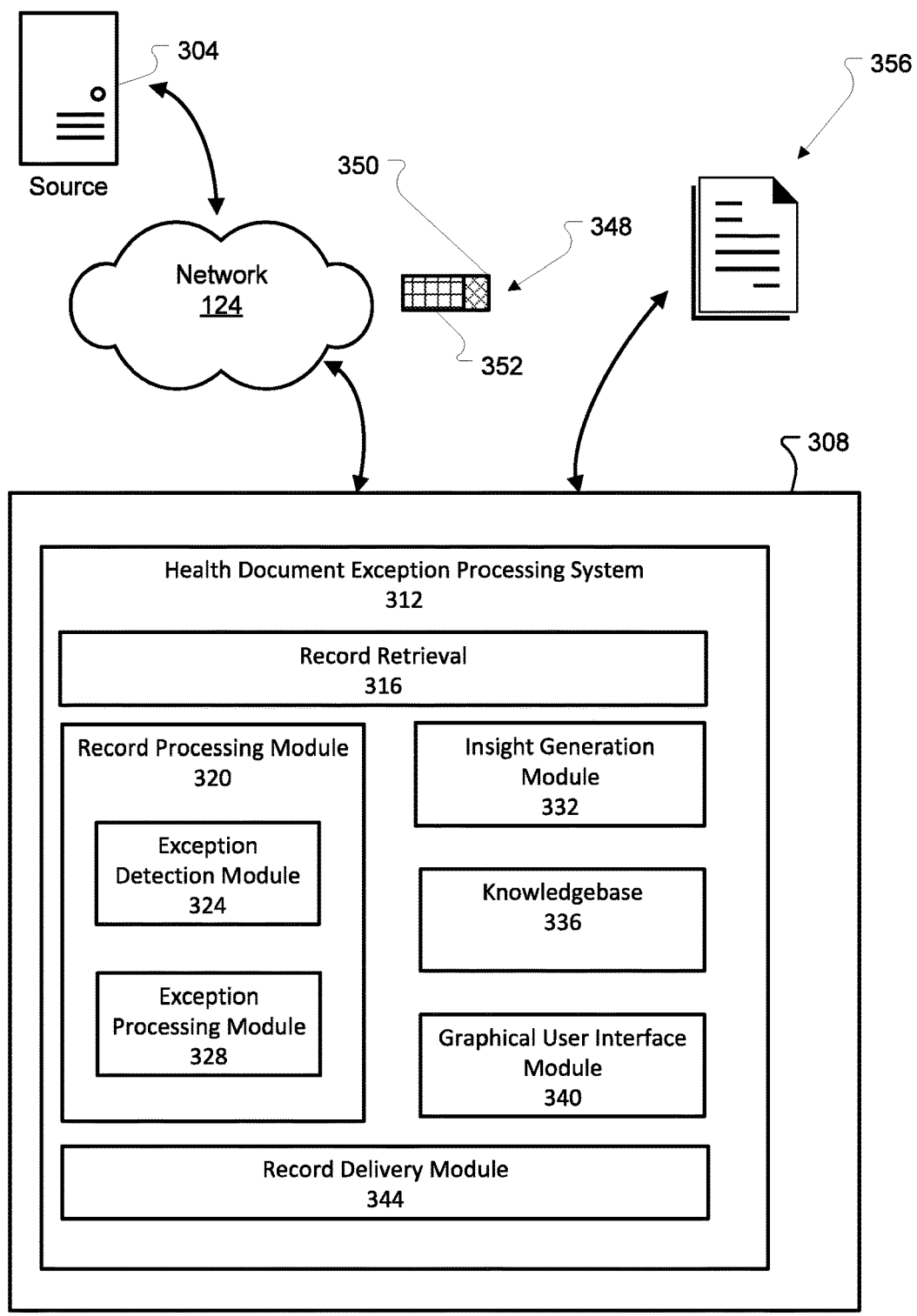
FIG. 3 depicts additional details of a health document exception processing system in accordance with examples of the present disclosure.

FIG. 3 depicts additional details of a health records system 308 including a health document exceptions processing system 312. The health document exceptions processing system 312 may be the same as or similar to the health document exceptions system 108 as previously described and may operate and/or function in a similar manner. In accordance with at least one example of the present disclosure, a target, or requester, 304 may initiate or otherwise make a request to the health document exceptions processing system 312 via the network 124. The record retrieval and acquisition module 316 may interact with the source 304 to assemble and submit a request for a record to be retrieved such that the record may be processed by the health document exception processing system 312. As further depicted in FIG. 3, a record 348 may be retrieved, where the record may include a header portion 350 and a body or package portion 352. In some instances, an exception may occur during the request and/or retrieval of the record from the source 304. If the exception happens during the request for the data, the processing of the exception may follow a same or similar workflow for exception processing for retrieved records and record elements, which are described below. When an exception occurs during processing on the content of the record, including natural language processing or other machine learning techniques, the processing of the exception may follow the same general workflow for exception processing for retrieved records and record elements.

Once a record has been retrieved by the record retrieval module 316, the health document exception processing system 312 may proceed to process the record at the record processing module 320. The record processing module 320 may detect exceptions at the record level or at the record element level utilizing an exception detection module 324. If an exception is detected, the exception detection module 324 may interact with the insight generation module 332, where the insight generation module 332 may generate or otherwise provide one or more suggestions for remedying the identified exception. For example, the insight generation module 332 may determine that a data or value associated with an element should be within a certain range. Based on previous responses, input, or modifications made by one or more users and accessible from a knowledgebase 336, the insight generation module 332 may provide a recommended conversion, for example, from Celsius to Fahrenheit.

The exception processing module 328 may normalize one or more records or one or more elements according to a configuration and/or rule, which may have been modified by actions of an operator based on one or more insights provided by the insight generation module 332. The graphical user interface module 340 may provide to a display, the one or more recommendations and/or accounting of changes and/or conversion made to the health record and/or one or more data portions associated with the health record. Accordingly, the graphical user interface module 340 may provide an interaction pathway for a user to accept, change, or deny one or more recommend changes suggested by the insight generation module 332. Thus, the graphical user interface module 340 may be used by the operator to review exceptions and insights and take actions based on the generated insights, which may modify the system configuration, rules or code within other modules. When the health record has been processed completely by the record processing module 320, which in some cases may include one or more passes, in parallel or serial processing and/or combinations thereof, the normalized health record may be delivered to the recipient who requested the record by the record delivery module 344. The record delivery module 344 may cause the health record to be assembled into a format for delivery by various means, such as but not limited to, secure file transfer protocol (SFTP), HL7 V2, a standard FHIR interface or a custom web service.

FIG. 4 depicts example exceptions 400 which may be identified and then processed by the health document exception processing system 108/312. More specifically, the exceptions 400 may be included as a table and/or stored in a location, such as a database, and the exceptions 400 may include an exception 404 and an insight 408 for potentially resolving the identified exception. More specifically, the exception 404 may be specific to a record, protocol, process, or data element and may apply to various levels of the health record retrieval and storage process. For example, during a record processing operation, the record processing module 320 may determine that a mapping of an element in the record does not exist or could not be found. For instance, a health record may include an element for a specific datatype, such as a form of a numerical value (e.g., double, integer, long, real, etc.). During a record processing operation, the exception detection module 324 may determine that instead of an expected or anticipated numerical value, a text value is received, retrieved, or otherwise obtained. That is, the exception detection module 324 may compare, match, or otherwise determine an expected or anticipated value, element, data, or otherwise from a template for example, and raise an exception if the obtained value does not match, meet, or otherwise comply with an expected or anticipated value. The exception detection module may create, or otherwise cause to be created, a record of the exception and record enough information about the exception to support an insight generation from the insight generation module 332. Based on the exception, an insight 408 may be obtained. Continuing with the above example, the insight generation module 332 may access the knowledgebase 336 to obtain and/or create an insight 408. Accordingly, the health document exception processing system 312 may cause the graphical user interface module 340 to generate a graphical user interface including the insight 408 and provide the insight 408 to an operator. For example, an insight indicative of the type/format suggestion corresponding to the element data type/format exception may be provided to a user. That is, a user may accept a recommended insight to modify the data element associated with the exception.

Additional details of an exception corresponding to a range exception 412 are depicted in accordance with examples of the present disclosure. More specifically, the range exception 412 may include one or more exception types 416 associated with a range element. For example, the range exception 412 may include range templates, items, elements, or other evaluative factors for evaluating a range element of a health record; such information may be provided from the knowledgebase 420, which may be the same as or similar to the knowledgebase 336. Non-limiting examples of an evaluative factor include context matching, element identification, range identification, and/or element comparison to determine one or more exceptions to be raised. Context matching may refer to whether or not a data element matches a specific range context—for example, a medication portion of a health record may include medication taken, either currently or in the past, by a patient—however, based on a patient's condition, the medication dosing is out of a typical range by one or more standard deviations. Element identification may include exception processing related to specific ranges for an element, for example, if an element is identified as a temperature, an exception may be raised if a received temperature is outside a specified element range. Similarly, a range identification may include exception processing related to determining whether an expected input falls within an expected range for a specific data type—for example, whether a medication dosage is provided in micrograms vs. milliliters. Similarly, an element comparison may compare one or more elements to one another to determine if an exception should be raised based on a range association with element; for example, if a heartrate associated with a patient a point in time was indicated as being within a normal range but a respiratory rate for the same point in time was significantly elevated. Of course, other exceptions related to range information may be provided and in some instances, one or more exceptions 404 may overlap with another exception 404.

In accordance with some examples of the present disclosure, the range exception types 416 may be utilized by the insights generation module 332 for determination of an insight based on the one or more exceptions 404 and/or one or more exception types 416. Accordingly, the exception types 416 may be provided and stored to the knowledgebase 336 for further processing. Moreover, once an operator has selected an action for remedying the raised exception, the remedy may be stored in the knowledgebase 420 such that subsequent insights may be based on an operator's accepted solution.

Figure 5:
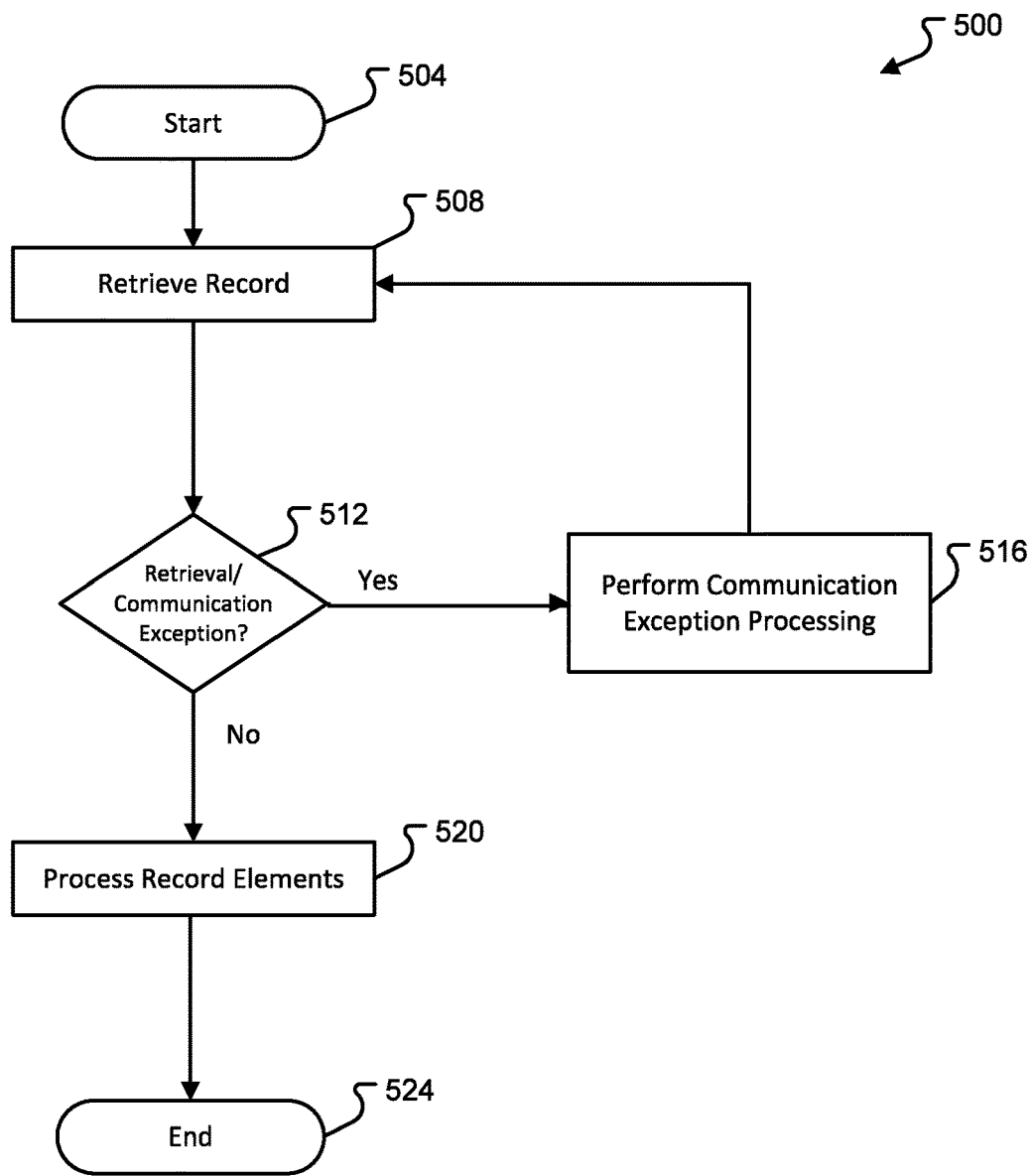
FIG. 5 depicts details of a first method in accordance with examples of the present disclosure.

In accordance with examples of the present disclosure, a method 500 for retrieving and processing a health record is provided. A general order for the steps of the method 500 is shown in FIG. 5. Generally, the method 500 starts with a start operation 504 and ends with the end operation 524. The method 500 may include more or fewer steps or may arrange the order of the steps differently than those shown in FIG. 5. The method 500 can be executed as a set of computer-executable instructions executed by a computer system and encoded or stored on a computer readable medium. Further, the method 500 can be performed by gates or circuits associated with a processor, Application Specific Integrated Circuit (ASIC), a field programmable gate array (FPGA), a system on chip (SOC), or other hardware device. Hereinafter, the method 500 shall be explained with reference to the systems, components, modules, software, data structures, user interfaces, etc. described in conjunction with FIGS. 1-4.

The method 500 starts at 504 and proceeds to 508 where an attempt to retrieve one or more records is made and one or more records may be retrieved. If an issue occurs due to a communication and/or retrieval exception, then the method 500 may proceed to 516 where specific communication exception processing of the exception may be performed. In accordance with some examples, the communication exception processing may resolve an exception automatically and/or require operator intervention. Once the exception has been resolved, a communication request for records may again be made at 508 such that a record may be received. The method may proceed to 520 where the record elements may be processed as described herein. Once all elements of all retrieved records are processed, the method 500 may end at 524.

Figure 6:
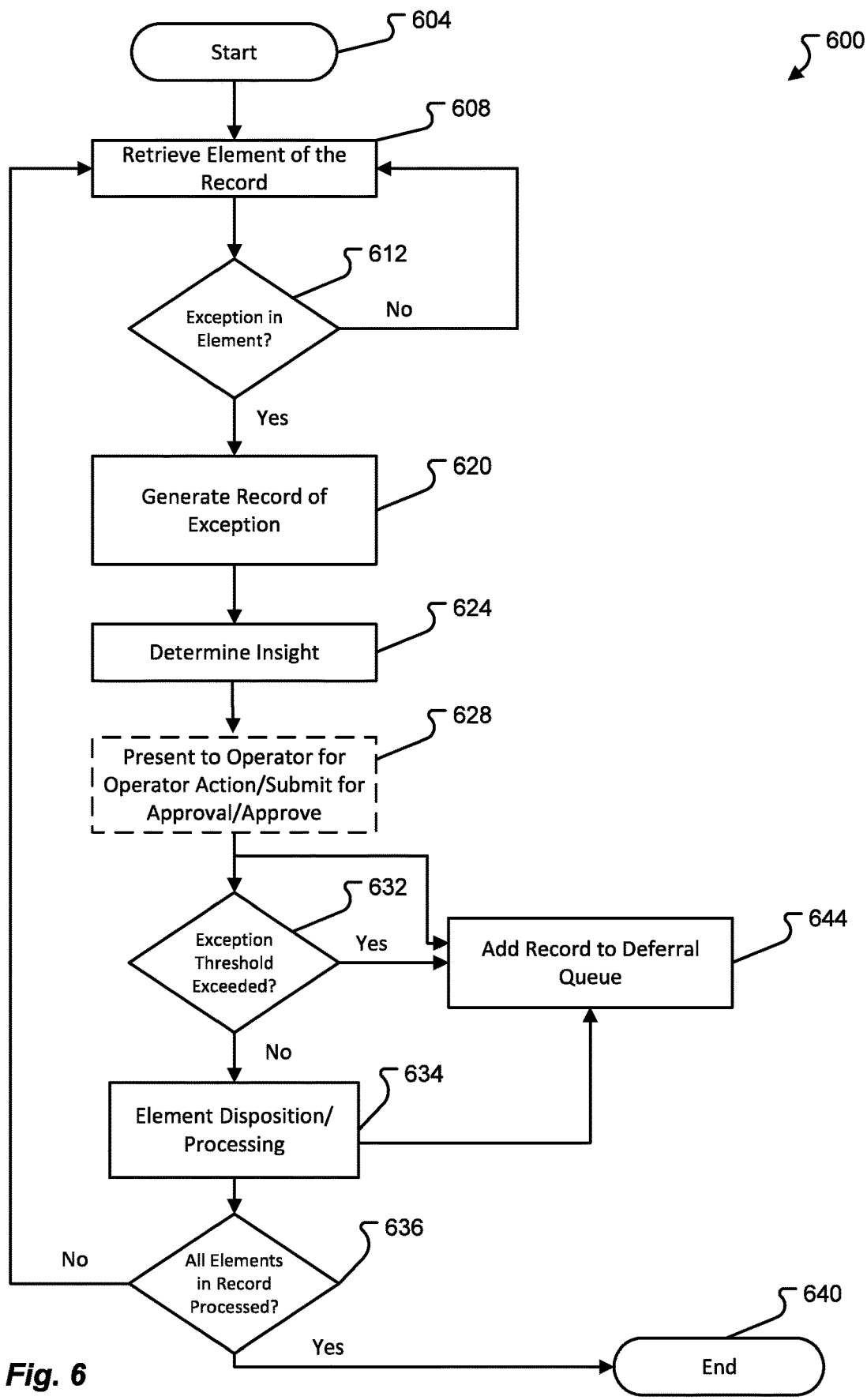
FIG. 6 depicts details of a second method in accordance with examples of the present disclosure.

In accordance with examples of the present disclosure, additional details directed to a method 600 for processing elements of a health record is provided. A general order for the steps of the method 600 is shown in FIG. 6. Generally, the method 600 starts with a start operation 604 and ends with the end operation 640. The method 600 may include more or fewer steps or may arrange the order of the steps differently than those shown in FIG. 6. The method 600 can be executed as a set of computer-executable instructions executed by a computer system and encoded or stored on a computer readable medium. Further, the method 600 can be performed by gates or circuits associated with a processor, Application Specific Integrated Circuit (ASIC), a field programmable gate array (FPGA), a system on chip (SOC), or other hardware device. Hereinafter, the method 600 shall be explained with reference to the systems, components, modules, software, data structures, user interfaces, etc. described in conjunction with FIGS. 1-5.

The method 600 starts at 604 and proceeds to 608 where one or more elements of a record is retrieved. That is, a request may be made to one or more data sources for a health record. In some examples, the health record may reside locally to the health document exception processing system. In some examples, the health record may reside at a location different from the health document exception processing system, for example at a health record custodian or other HIT vendor. At 612, the health document exception processing system may analyze the health record to determine if one or more exceptions are present. More specifically, unprocessed elements within the health record may be processed to determine if one or more of the following non-limiting exceptions exist: the data in a health record document associated with the health record may not be in the expected forma; the data in one or elements may be mis-formatted, a field in a record that is expected to hold a number instead holds an array of numbers; the label of a field is incorrect due to a transcription error, OCR scanning error or a typo. For example; a date field includes an unexpended format; an identifier, such as taxpayer identification number, credit card number, state driver's license number, insurance subscriber identity number, national provider identifier and/or other identifying codes may be mis-formatted in general or in the specific expectation for a particular identity issuer such as a state, a health system, or insurance company; an expected field may be absent or contain an unreadable element; an object may contain an unexpected data element or data type—for example, an extra data element and/or extra data type; the value of an element of the document may be out of the expected range or in unknown units; the name of an element might not match the expected code, such as an object identifier, for that type of field; a medical diagnosis code value may not match the purported code set of that element; an element of the record may contain out-of-range data (a negative BMI, diastolic blood pressure greater than systolic blood pressure, etc. . . . ); a particular element is expected in a record and required for the next stage of processing, but cannot be found or extracted; a process for indexing a document for subsequence search may be an exception if the elements of the document that must be indexed to create the desired indices for the source documents cannot be indexed; and an exception if requirement elements of a document do not yield the required metadata, a process for extracting metadata for that document may yield an exception. In some instances, a given patient record and a different use case may alter or change what is considered to be an exception and what is not considered to be an exception. For example, requirements of a document prepared for coding for Medicare risk adjustment may require a diagnosis and supporting documentation in a record; thus the absence of or other issues with this particular type of record may be an exception. However, diagnosis elements could be optional, but correct service codes, like CPT codes from the American Medical Association, would be imperative in a medical claims use case, where the absence of or ill formatting of these service elements would present an exception. In the case where certain data values are discrete data that are represented with values from a shared code system or ontology, we may refer to these as "coded concepts". In healthcare, some examples of code systems include SNOMED CT, RxNorm, LOINC, ICD-9-CM, ICD-10-CM, and Hierarchical Chronic Conditions (HCC). Other exceptions are contemplated; an exception may exist that encompasses any other kind of information related to an object or a document that cannot, by default, be handled by a particular system handling data extracted from EMR and other HIT systems. The presence of an element may imply the presence or absence of one or more additional elements, just as the absence of an element may imply the absence or presence of one or more additional elements. In some such cases the system will know by rule that an element is absent; in other cases the system may suspect that an element is missing based on the absence or presence of one or more additional elements and/or their values.

If the health document exception processing system 312 detects an exception in a document element, the system may generate a record of the exception at 620, recording enough information about the exception to provide such information to the insight generation module 332 and subsequent resolution processes. The method 600 may then proceed to 624, where the insight generation module 332 may determine a nature of the exception, and propose one or more insights, suggestions, or otherwise to present to an operator at 628. Examples of exceptions and possible actionable insights may include those listed in Table 1 and similarly FIG. 4.

TABLE 1

| Exceptions | Insights |
|---|---|
| No currently existing mapping for element name (elements:= data type, data format, name) | Substring, synonym, NLP match suggestion |

TABLE 1-continued

| Exceptions | Insights |
|---|---|
| Element (known name) exceptional data type/format | Type/format determined by system: suggest accept this format/convert to accepted format<br>Ask operator to determine format for accept/convert |
| Atypical units (Euros not Dollars, degrees Rankin not degrees Celsius) | Suggest units accept/conversion to typical units |
| Value out of range (percentage >100%, negative BMI, medical code not found in code set, . . . ) | If out of range because of wrong units: suggest conversion |
| Lack of data provenance for record or section of record | Update rules for determining data provenance<br>Generate request to original custodian of data for correct provenance |
| The indices for the record cannot be built | Manual update to indexing rules to account for novel data is suggested<br>Include as-is |
| There is evidence of a document in an external system that cannot be obtained (for example, a scanned image in a DMS) | Ask operator to get access to the external document and let the system append it to the record |
| Other exceptions | Manual rules change suggested<br>Elide element<br>Replace element with a placeholder string or template<br>Include as-is, as extracted |

Other exceptions include missing required data elements or content. For example, in some contexts or use cases, missing optional elements or content could be considered an exception. These example exception classes and insights are provided for the purpose of illustration and are not meant to limit the behavior of the system.

As provided above, exceptions may exist for cases where there is no mapping for the name of an element that is known to the system. For example, the system may be processing a Fast Healthcare Interoperability Resources (FHIR) record that contains an observation element named "GCS." The observation element may not be an element name known to the system configuration for processing. The insight generation module 332 may utilize a variety of well-known computer science techniques, including but not limited to, substring matching, dictionary table look up of synonyms, and natural language processing (NLP) techniques to suggest an element name known to the health document exception processing system 312 for example. Thus, for example, a synonym lookup for "GCS" may return "Glasgow Coma Scale" which is subsequently matched to the FHIR element name "glasgow" by a subsequent FHIR lookup. The insight generation module 332, together with the knowledgebase 336, may provide a suggestion to an operator via the graphical user interface module 340 to create a mapping for such an element type from an unknown name "GCS" to "glasgow". Accordingly, future detections of GCS may result in an exception where the insight generation module 332 may reference the knowledgebase 336 directly such that additional processing associated with a synonym lookup process and subsequent mapping is not required to be completed. Rather, the knowledgebase 336 may provide the insight generation model 332 an indication that GCS refers to "glasgow" and such insight may be provided to the operator sans the additional mapping suggestion.

As additionally provided above, exceptions directed to a name of an element may be known to the system, but a data type or format of the element is unprecedented. For example, the data type or format may be labeled incorrectly, but the health document exception processing system 312 may infer an actual format for the element and generate an insight that suggests that the operator assign the inferred format to the data in this element. The health document exception processing system may generate an insight that maps from this incorrectly identified format to the correct format when this combination of misidentified format and inferred format are detected. For example, an element may identify the format of the data in the element as XML format when the format is actually JSON format. Another insight that may be generated by the system for these types of exceptions is to instruct the operator to determine the actual format or data type for the unprecedented format or data type in the element and to create a new mapping. For example, the element may be presented to an operator via the graphical user interface module 340; absent an insight as to an inferred mapping, the operator may be required to manually map the element to a specified format.

In some examples, exceptions exist where the record element includes discrete data that has units of measurement that is atypical in nature. For example, if the health document exception processing system 312 generally receives temperature measurements for body temperature in degrees Celsius, but the data element unit type is degrees Rankine, the health document exception processing system 312 may generate an insight suggesting that the operator convert the element value into the appropriate Celsius value and convert the measurable unit of the element to degrees Celsius. In another case, the data element for this data type may normally have a single value, but in this instance, it contains a list of values. An insight may be generated that suggests to the operator to use the first value in the list and produce a single value in this element. Alternatively, or in addition, an insight may be provided to an operator suggesting that the operator request a change in the source code, script, or otherwise of the system to support arrays for this data type.

In some instances, an exception may be raised where the data value is out of range. The health document exception processing system 312 may be configured with acceptable thresholds for certain data types. For example, a person cannot have a negative body mass index (BMI), an instance where a medical code for a diagnosis may not exist in a reported code set, a percentage may be reported over 100 percent, or a body temperature may be below a reasonable human value. These types of data may raise an exception when such ranges, or thresholds, are exceeded. In some instances, the health document exception processing system 312 may provide a suggestion to replace the out of bound value with a boilerplate message indicating that unreliable data was extracted. In some instances, the health document exception processing system 312 may provide an insight to change units for data if it appears that the unit type was mistaken. For example, where degrees Fahrenheit rather than degrees Celsius for a body temperature measurement made in Celsius is used, if the temperature reading is in bounds for units of type Celsius, then the insight generation module 332 may generate an insight to suggest to the operator to correct the units to degrees Celsius.

In some examples, an exception may be detected where the provenance of the data cannot be determined for a record or a section or element of a record. In such instances, the data provenance determination rules may need to be updated. In some instances, an operator may need to query the original custodian of the data for the correct data provenance for the record or record section. Accordingly, the insight generation module 332 may generate a suggestion to be provided to the operator to make such inquiry. In some instances, the inquiry is automatically generated by the health document exception process system and may be automatically provided to such custodian. In some examples, an exception may be detected when the identity of the patient or the healthcare provider or the insurance plan member or the custodian of the healthcare document or the current or proposed future custodian of the healthcare document cannot be identified or verified or considered trusted by the system. In an example, while the proposed custodian of a document may be identified to the system, they might not be known to the system as a trusted custodian of the healthcare documents, which would generate an exception.

In some examples, an exception may be raised when indices cannot be generated for a record, section, or element of a record. For example, if the indexing template expects a date type of value but encounters a string containing a substring that can be converted to a date, an exception may be provided. However, such processing rules may be updated such that the exception can be overcome. For example, one or more processing rules may be updated to covert a date of type string to a date corresponding to a specific data format, such as DD/MM/YYYY.

In instances where a useful insight cannot be generated for an exception, the health document exception processing system 312 may generate an insight with a suggestion to an operator to manually change a processing rule. For example, where a data format does not match an expected format, the health document exception processing system provide an exception indicating that a mismatch occurs and that additional intervention from an operator is needed.

Once the operator has been presented with an insight or suggestion via the graphical user interface module 340, the operator may select one or more presented options for proceeding at 628 for example. For example, the operator may accept a recommended suggestion associated with an insight and/or provided by the insight generation module 332, may perform manual changes to the health document processing system, may submit a request for a system code change, and/or may "park" the record or document that includes the exception for reprocessing after one or more other changes are made at 644.

In some examples, the operator may act on insights as they are generated, act on groups of insights, or act on all insights for an entire document or record. In some instances, the exception processing method 600 may include one or more thresholds for an amount of exceptions that may be raised on a per document or per record basis; should the threshold be exceeded, the method 600 may proceed to 634 such that additional exceptions and/or insights are parked in a deferral queue at 644 should unprocessed exceptions and/or record elements exist that have yet to be processed due to exceeding the threshold. Such documents added to the deferral queue may be reprocessed by the system at a subsequent time, based on rules (time elapsed, updated applied, issue tickets closed, operator intervention, etc. Alternatively, or in addition, at 634, the method 600 may perform exception processing in accordance with one or more insights. That is, if an insight is accepted, either explicitly by an operator or as part of the data processing rules of the health document exception processing system, the exception is then processed. If additional record elements or exceptions exist for further processing, the method may proceed to 608 where additional elements are retrieved for further processing.

Figure 7:
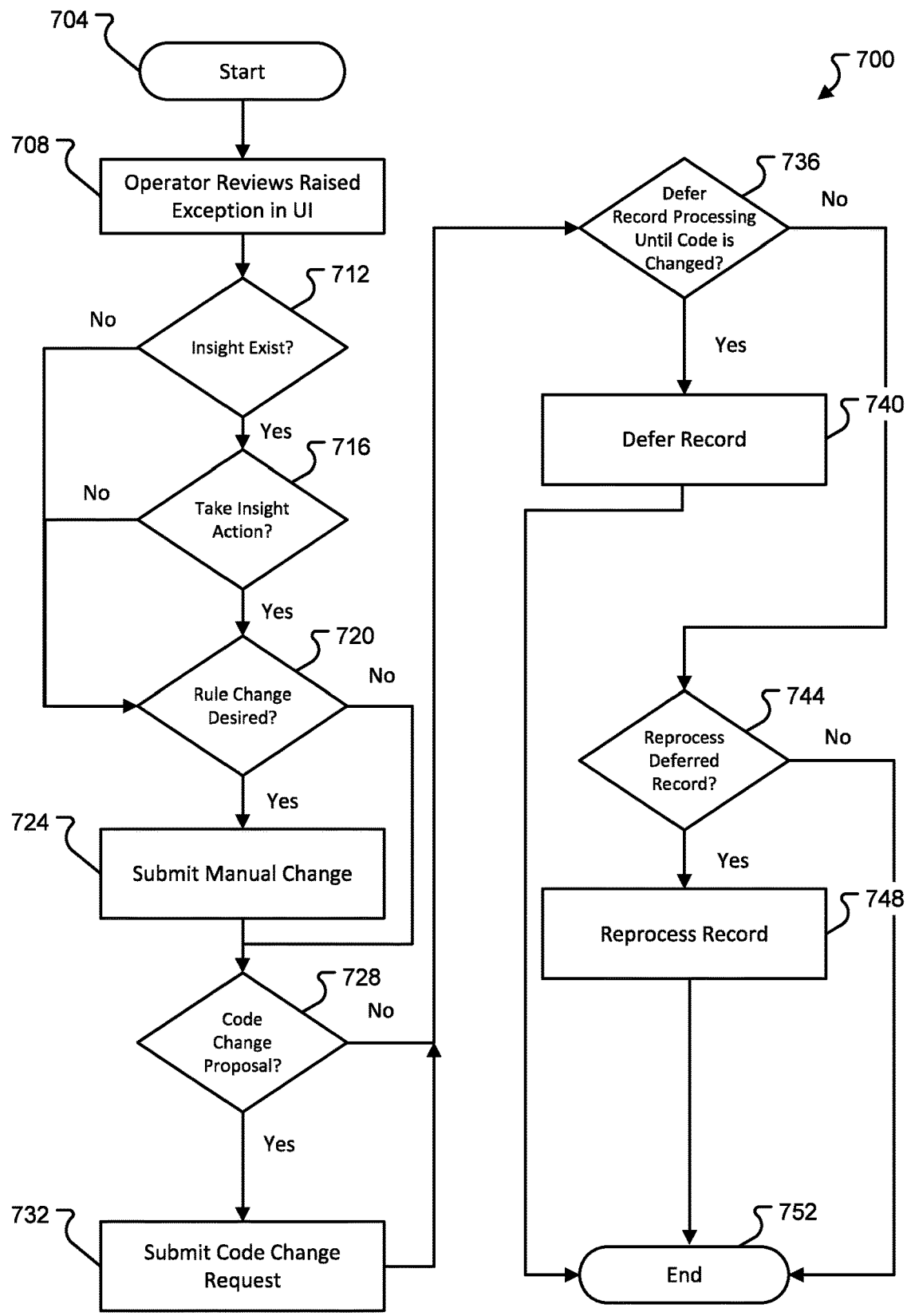
FIG. 7 depicts details of a third method in accordance with examples of the present disclosure.

FIG. 7 depicts additional details directed to a method 700 for insight review and subsequent processing. A general order for the steps of the method 700 is shown in FIG. 7.

Generally, the method 700 starts with a start operation 704 and ends with the end operation 752. The method 700 may include more or fewer steps or may arrange the order of the steps differently than those shown in FIG. 7. The method 700 can be executed as a set of computer-executable instructions executed by a computer system and encoded or stored on a computer readable medium. Further, the method 700 can be performed by gates or circuits associated with a processor, Application Specific Integrated Circuit (ASIC), a field programmable gate array (FPGA), a system on chip (SOC), or other hardware device. Hereinafter, the method 700 shall be explained with reference to the systems, components, modules, software, data structures, user interfaces, etc. described in conjunction with FIGS. 1-6.

The method 700 starts at 704 and proceeds to 708 where an operator may be provided one or more insights and/or exceptions for review. In some examples, the method 700 may be performed without operator intervention and may be performed by the health document exception processing system 312. Alternatively, or in addition, the operator may review the insights in a GUI produced by the graphical user interface module 340. For example, the operator may be provided with a plurality of operations to act on the insights, perform manual changes to the system configuration/rules/data, and submit a request for code changes and optionally "park" a record or document for reprocessing after other changes are made.

In some examples, the operator may act on insights as presented by the graphical user interface module 340. Accordingly, if an insight exists at 712, the operator, or system, may take an action, often a recommended action, at 716 and such taken action will be implemented for the particular element that raised the exception. Whether or not the operator accepts the insight action at 716, the operator is provided an option to add a manual change to the configuration/rules of the system at 720. In some instances, a rule change may be desired and the operator may determine that a rule change should be made to the manner in which at least one element is processed for the health record. Accordingly, the method 700 may proceed to 724 where a manual rule change may be submitted and/or implemented. In some instances, the operator is prompted to optionally propose code changes to the system software(/firmware/hardware) at 728. If the operator choses to submit a code change, the code change may be formally submitted 732.

Regardless of whether or not an operator chooses to submit a code change request at 724 and/or 732, the operator may have the option of deferring one or more health records for further processing at 736. If the operator defers one or more records at 740, the system prompts the operator to reprocess the deferred record at a future time, or optionally automatically reprocess the record when an amount of time has elapsed or a code update has been made and detected. In some instances, other criteria may dictate when such deferred record is to be reprocessed. If the operator chooses not to defer the record at 736, the method 700 may proceed to 744 where the non-deferred record may be processed and/or reprocessed at 748. The method 700 may end at 752. In some examples, the method depicted in FIG. 7 may be utilized to train a machine learning system for "intelligent exception handling", which can augment or replace the operator handling of exceptions, as well as provide feedback and training to the insight generation module 332. Accordingly, each of the actions taken within FIG. 7 may be recorded and provided to a machine learning module for further processing, training, and optimization.

FIG. 8 depicts at least one example of a graphical user interface provided by the graphical user interface module 322 in accordance with examples of the present disclosure. More specifically, the insight generation module 332 may provide an insight to convert the temperature element 212 of the medical record portion 208 of the medical record 204 to 96.8. As one example, the health document exception processing system may determine that the element value of 36 may correspond to one or more exceptions based on a difference in units and/or range. Accordingly, the insight generation module 332 may access the knowledgebase 336 to determine whether a temperature reading of 36 corresponds to a standard temperature value and/or whether a conversion processing template and/or conversion processing rules exist. If such rules exist, the health document exception processing module may provide a suggestion to convert 36 to 98.6. Accordingly, the insight generation module 332 may provide the insight, or recommendation, to the graphical user interface module 340 for display to an operator. Accordingly, the graphical user interface of FIG. 8 may display a menu item of a suggested change and/or other action for an operator to utilize. The suggestion displayed in FIG. 8 generally corresponds to a single element having been identified as an exception. Accordingly, a next exception and suggestion may be provided to an operator after an operator selects an appropriate option.

FIG. 9 provides additional details of a data structure 900 in accordance with examples of the present disclosure. The data structure 900 may be provided as a record of identified exceptions together with details and an ultimate action that is accepted or taken. The data structure may include an exception ID element 904, an exception detail element 908, and an action taken element 912. For example, a first exception may be identified by an exception ID of 12A7F; additional details of the specific exception may be found at or by an entry corresponding to 01. In some instances, 01 may correspond to a predetermined category of an exception and/or a specific exception. For example, 01 may refer to an exception indicating that an issue with units for a specific element was identified. Moreover, the action taken at 912 may indicate that a suggested action was accepted or otherwise taken.

Figure 10:
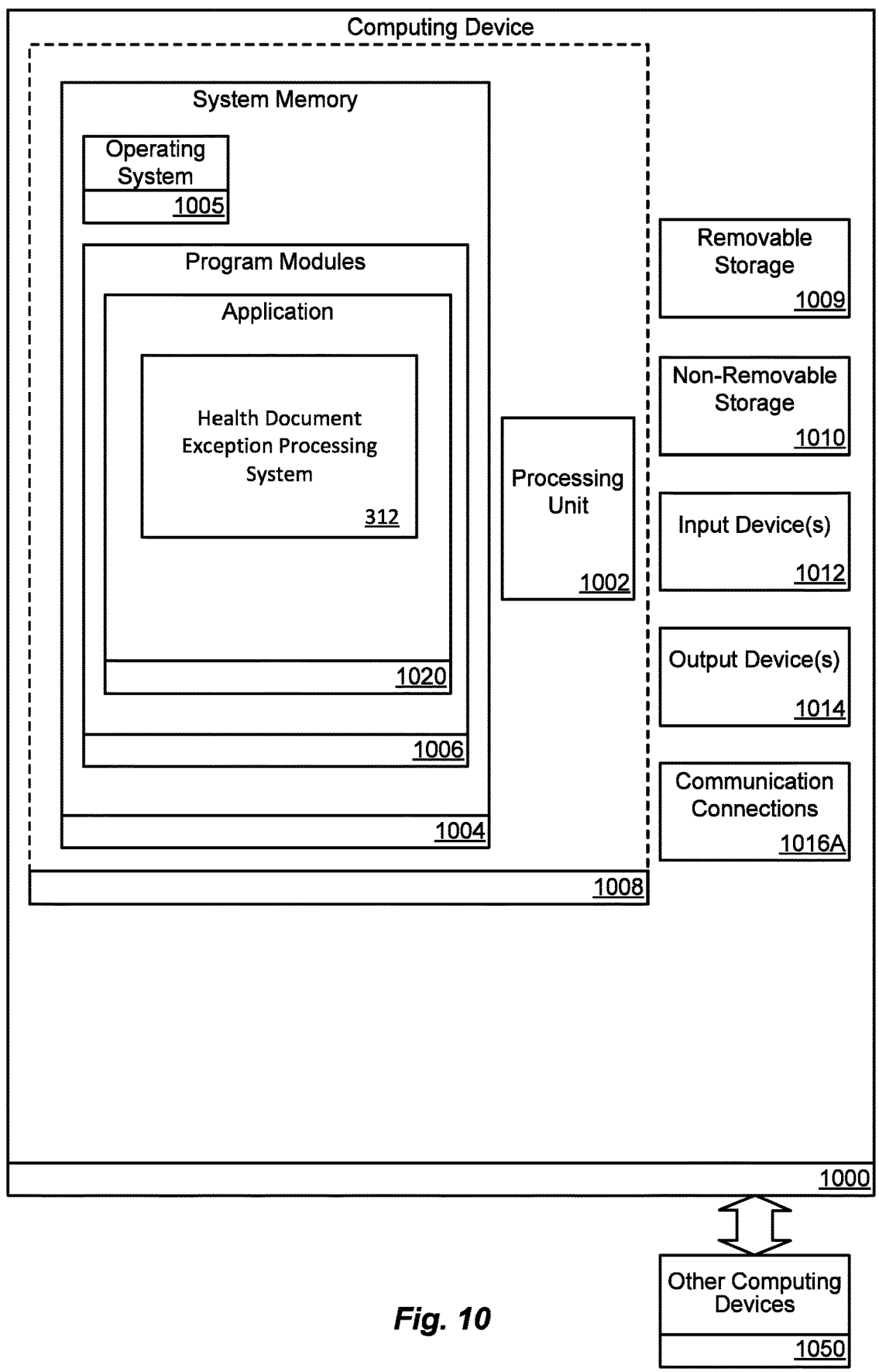
FIG. 10 depicts a simplified block diagram of a computing device with which aspects of the present disclosure may be practiced.

FIG. 10 is a block diagram illustrating physical components (e.g., hardware) of a computing device 1000 with which aspects of the disclosure may be practiced. The computing device components described below may be suitable for the computing devices, such as the health document expansion retrieval system, and/or one or more endpoints associated with the requester and/or one or more sources. In a basic configuration, the computing device 1000 may include at least one processing unit 1002 and a system memory 1004. Depending on the configuration and type of computing device, the system memory 1004 may comprise, but is not limited to, volatile storage (e.g., random access memory), non-volatile storage (e.g., read-only memory), flash memory, or any combination of such memories. The system memory 1004 may include an operating system 1005 and one or more program modules 1006 suitable for performing the various aspects disclosed herein such as the authenticator, the health document analyzer, the health document source discovery processors, the health document assembler, the health document eligibility controller, and one or more workflows associated with FIGS. 4-7. The operating system 1005, for example, may be suitable for controlling the operation of the computing device 1000. Furthermore, aspects of the disclosure may be practiced in conjunction with a graphics library, other operating systems, or any other application program and is not limited to any particular application or system. This basic configuration is illustrated in FIG. 10 by those components within a dashed line 1008. The computing device 1000 may have additional features or functionality. For example, the computing device 1000 may also include additional data storage devices (removable and/or non-removable) such as, for example, magnetic disks, optical disks, or tape. Such additional storage is illustrated in FIG. 10 by a removable storage device 1009 and a non-removable storage device 1010.

As stated above, a number of program modules and data files may be stored in the system memory 1004. While executing on the processing unit 1002, the program modules 1006 (e.g., one or more applications 1020) may perform processes including, but not limited to, the aspects, as described herein. Other program modules that may be used in accordance with aspects of the present disclosure may include electronic mail and contacts applications, word processing applications, spreadsheet applications, database applications, slide presentation applications, drawing or computer-aided application programs, etc.

Furthermore, aspects of the disclosure may be practiced in an electrical circuit comprising discrete electronic elements, packaged or integrated electronic chips containing logic gates, a circuit utilizing a microprocessor, or on a single chip containing electronic elements or microprocessors. For example, aspects of the disclosure may be practiced via a system-on-a-chip (SOC) where each or many of the components illustrated in FIG. 10 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 1000 on the single integrated circuit (chip). Aspects of the disclosure may also be practiced using other technologies capable of performing logical operations such as, for example, AND, OR, and NOT, including but not limited to mechanical, optical, fluidic, and quantum technologies. In addition, aspects of the disclosure may be practiced within a general-purpose computer or in any other circuits or systems.

The computing device 1000 may also have one or more input device(s) 1012 such as a keyboard, a mouse, a pen, a sound or voice input device, a touch or swipe input device, etc. The output device(s) 1014 such as a display, speakers, a printer, etc. may also be included. The aforementioned devices are examples and others may be used. The computing device 1000 may include one or more communication connections 1016A allowing communications with other computing devices 1050. Examples of suitable communication connections 1016A include, but are not limited to, radio frequency (RF) transmitter, receiver, and/or transceiver circuitry; universal serial bus (USB), parallel, network interface card, and/or serial ports.

Figure 11:
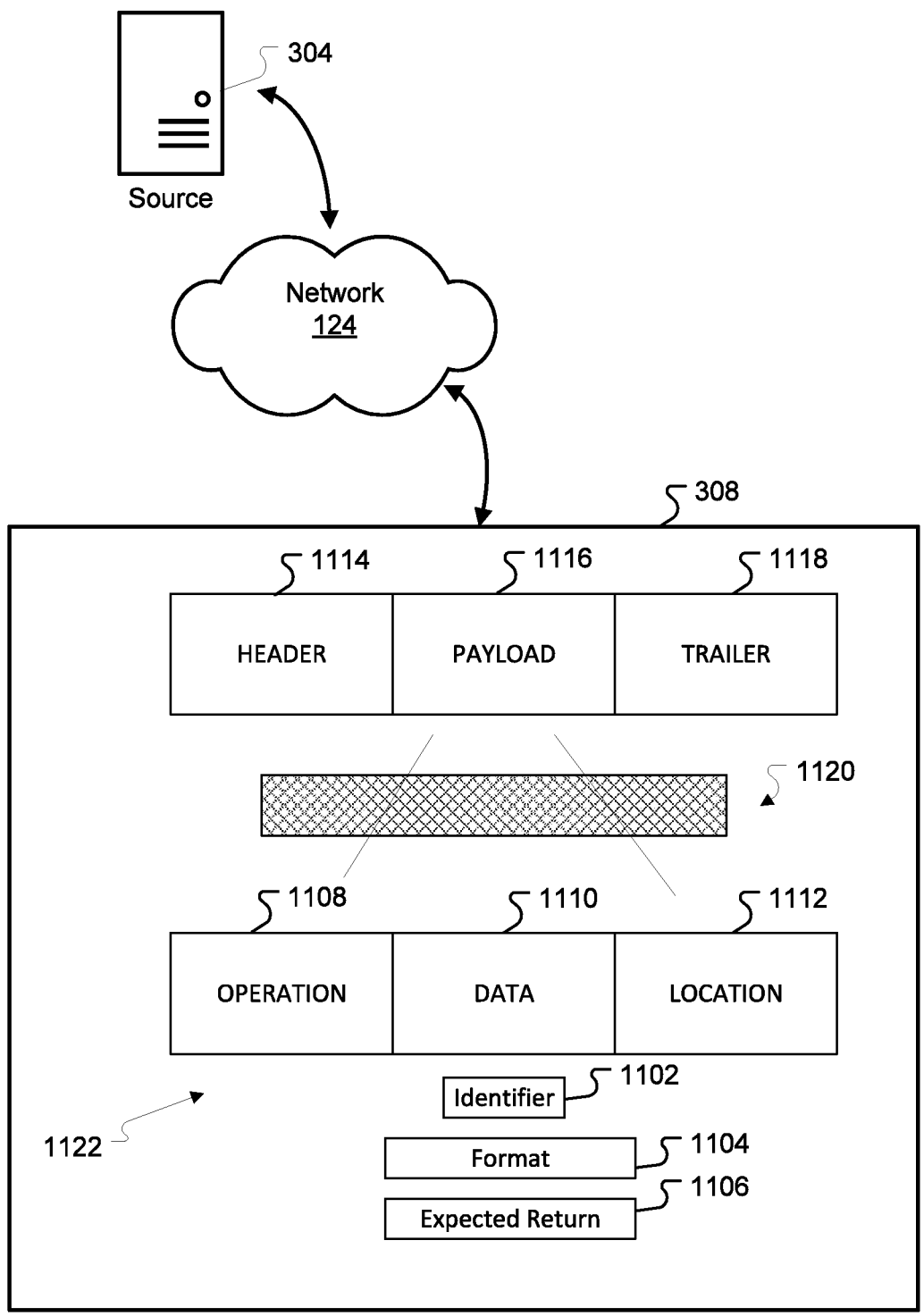
FIG. 11 depicts details directed to communication exception process in accordance with examples of the present disclosure.

The term computer readable media as used herein may include computer storage media. Computer storage media may include volatile and nonvolatile, removable and non-removable media implemented in any method or technology for storage of information, such as computer readable instructions, data structures, or program modules. The system memory 1004, the removable storage device 1009, and the non-removable storage device 1010 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1000. Any such computer storage media may be part of the computing device 1000. Computer storage media does not include a carrier wave or other propagated or modulated data signal. FIG. 11 depicts additional details with respect to one or more communication exceptions that may occur when retrieving an electronic health record. The health document processing system 308 may formulate a request to retrieve one or more records from a custodian of electronic records as previously described. While documentation generally exists for establishing communication sessions between parties transferring information from one party to another party, communication between parties is not always without error. For example, some interfaces may require a communication session to be established prior to servicing a request for a digital healthcare record. In some instances, a session may time out, or become stale, and require one or more systems to reconnect or otherwise reestablish a communication session. Other stateless methods of transferring information, such as utilizing a web application programming interface, may also present issues should a commonly utilized specification or protocol be updated, changed, or otherwise present differently between two devices attempting to connect to one another.

The information exchanged between devices through networks or between applications may be governed by rules and conventions that generally conform to one or more communication protocols. A communication protocol is a system of rules that allow two or more entities of a communications system to transmit information via any kind of variation of a physical quantity. The protocol defines the rules, syntax, semantics and synchronization of communication and possible error recovery methods. In accordance with examples of the present disclosure, a communication protocol, or a series of protocols, may be analyzed by at least one component of the health document exception processing system prior to data transmission. For example, a destination, based on address, such as but not limited IP address, network address, or the like, may be compared against known and/or previously utilized communication protocols known to work and/or explicitly provided by a destination system. Should data assembled in accordance with one or more communication protocols not match a destination protocol, the record retrieval module 316 for example, may cause an insight, or prompt, to be provided to a user prior to sending or attempting communication with the destination system. In some examples, a response indicating that a communication and/or communication attempt was not valid may be indicative of an exception. For example, a lack of an acknowledgement by a destination system may indicate that the communication attempt failed. Further, the analysis of a communication protocol is not limited to communications between two or more systems. In some examples, an operation or process to save, create, or modify, or retrieve a health record may be analyzed for compliance with a known health record format. Thus, for instance, a protocol or standard residing in another protocol or standard may be analyzed for compliance.

As depicted in FIG. 11, a request to perform some operation related to an electronic health record or document may be assembled as the electronic health document processing system 308. The request may include an identifier 1102, a format 1104 of the request, and an expected return 1106. The identifier 1102 may identify an electronic health record, for example, by patient identifier number or other unique identifier assigned to an electronic health record. The format 1104 may correspond to a format of the request and may be compared to known request formats for various electronic health record custodians. Accordingly, based on the format, the electronic health document processing system 308 may expect a specific returned result 1106 provided by the custodian. In some instances, the expected return 1106 corresponds to an acknowledgement. In some instances, the expected return 106 may correspond to an electronic health record or a portion thereof.

In some instances, a request for a record may require a requesting system to provide information related to an operation 1108 (retrieve, update, change, save, etc.) to be performed with respect to the electronic health record, any data, data type, format, or the like that the request is requesting, and in some instances, a location 1112 specifying a location, custodian, or otherwise of the electronic record. The requested components may be encrypted at 1120 and assembled into a communication format specific to one or more communication protocols. In some examples, the header 1114, the payload 1116, and/or the trailer 1118 may be assembled and sent electronically to a custodian 304 via the network 124. In accordance with examples of the present disclosure, prior to sending the request to the source 304, the request may be vetted against known good standards and/or other communication protocols. Accordingly, should an exception occur before a communication is sent, an operator may receive an insight indicating that the message does not comply with one or more communication standards or protocols—at which point, the operator may resolve such issue or otherwise initiate a resolution process.

In some examples, the source 304 may provide a return message that does not comply with one or more established communications standards and/or protocols. Accordingly, the health document exception processing system 304 may receive data that is jumbled or otherwise not organized or arranged in a desired format. In some instances, a health document exception processing system may generate an insight based on the returned information in an attempt to notify an operator of a possible communication issue resolution. In other instances, and based on the generated insight, one or more various communications formats may be changed, updated, or modified based on known working communication protocols. For example, if an initial request used a first protocol, a second or third request may utilize a different protocol.

Figure 12:
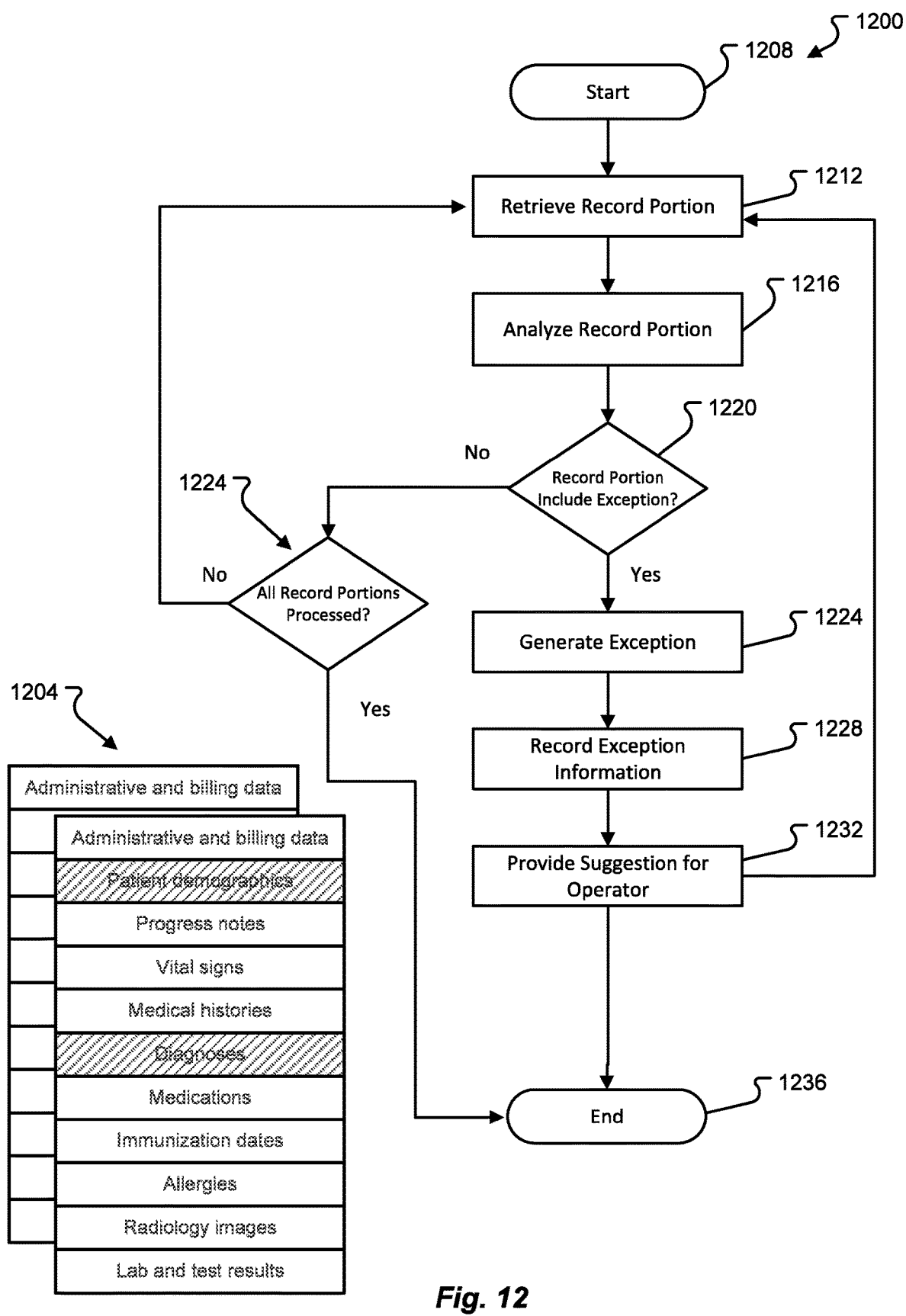
FIG. 12 depicts details of a fourth method in accordance with examples of the present disclosure.

FIG. 12 depicts one or more methods directed to processing one or more records in accordance with examples of the present disclosure. More specifically, an electronic health record 1204 may include various portions, such as but not limited those portions displayed in FIG. 12. In some instances, when record information is retrieved, the record information may be lacking one or more record portions. For example, the record 1204 may be missing a diagnosis and/or patient demographics portion. The reason for the missing portion could be for a variety of reasons; however, the electronic document exception processing system may utilize the available record information to assemble a health record. While noted as being absent, should a format or portion of the record change, the electronic document exception processing system may generate one or more insights to be provided to an operator to effect a rule change or other change when processing records received from the one or more specific record providers.

FIG. 12 further depicts additional details directed to a method 1200 for record portion processing in accordance with examples of the present disclosure. A general order for the steps of the method 1200 is shown in FIG. 12. Generally, the method 1200 starts with a start operation 1208 and ends with the end operation 1236. The method 1200 may include more or fewer steps or may arrange the order of the steps differently than those shown in FIG. 12. The method 1200 can be executed as a set of computer-executable instructions executed by a computer system and encoded or stored on a computer readable medium. Further, the method 1200 can be performed by gates or circuits associated with a processor, Application Specific Integrated Circuit (ASIC), a field programmable gate array (FPGA), a system on chip (SOC), or other hardware device. Hereinafter, the method 1200 shall be explained with reference to the systems, components, modules, software, data structures, user interfaces, etc. described in conjunction with FIGS. 1-11.

The method 1200 starts at 1208 and proceeds to 1212 where a record portion may be retrieved. Similar to method 600, method 1200 processes a record; however, method 1200 may operate at one level above the method 600, processing portions of a record without regard to specific elements of the record itself. That is, the method 1200 may generally process one or more records to determine if an entire record is preset, or if the specific record is missing one or more portions. Accordingly, the record is retrieved at 1212 and each portion may be analyzed at 1216. If an exception is identified at 1220, the method 1200 may proceed to 1224 where exception information may be generated and recorded at 1228. At 1232, one or more insights may be generated and provided to an operator. In some instances, the lack of a record portion may indicate that the record portion was not retrieved, does not exist, or otherwise is not available; as such, the system may direct the operator to retry a record retrieval operation to verify that such portion is not available and verify that a communication issue was not the reason for the missing portion. Further, an operator or the system itself, may note that the record lacks a specific portion; accordingly, future operations involving the missing portion may be avoided. If the record portions do not include or otherwise generate an exception at 1220, the method 1200 may processed to 1124 until all records have been processed. The method 1200 may end at 1236.

In accordance with examples of the present disclosure, a communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

In the foregoing description, for the purpose of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor (GPU or CPU) or logic circuits programmed with the instructions to perform the methods (FPGA). These machine-executable instructions may be stored on one or more machine-readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the examples. However, it will be understood by one of ordinary skill in the art that the examples may be practiced without these specific details.

Also, it is noted that the examples were described as a process, which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, examples may be implemented by hardware, software, firmware, middleware, microcode, hardware description languages, or any combination thereof. When implemented in software, firmware, middleware or microcode, the program code or code segments to perform the necessary tasks may be stored in a machine-readable medium, such as a storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In accordance with some examples of the present disclosure, a system is provided. The system may include at least one processor, and memory storing instructions that, when executed by the at least one processor, causes the system to perform a set of operations, the set of operations comprising receiving a portion of an digital healthcare record, analyzing the portion of the digital healthcare record for one or more exceptions, generating at least one insight based on the one or more exceptions, and causing the at least one insight to be displayed at a user interface of a display device.

At least one aspect of the above example includes where the one or more exceptions includes a received data value that is above or below a defined range. At least one aspect of the above example includes where the at least one insight displayed at the user interface of the display device provides a second data value based on the received data value that is out of range, the second data value being within the range. At least one aspect of the above example includes where the range is specific to a data type of the received data value. At least one aspect of the above example includes where the set of operations includes analyzing the portion of the digital healthcare record utilizing the second data value. At least one aspect of the above example includes where the set of operations includes receiving an indication to delay processing of the portion of the digital healthcare record. At least one aspect of the above example includes where the set of operations includes providing a proposed change to a processing rule associated with a data value included in the one or more exceptions. At least one aspect of the above example includes where the set of operations includes providing a proposed change to a processing rule associated with a data field included in the digital healthcare record. At least one aspect of the above example includes where the set of operations includes receiving an indication to accept the at least one insight to modify a data element associated with the one or more exceptions. At least one aspect of the above example includes where the set of operations includes detecting an incorrectly identified data format, and mapping the incorrectly identified data format to a correct data format. At least one aspect of the above example includes where the one or more exceptions includes at least one unexpected received data element and/or an unexpected received object property. At least one aspect of the above example includes where the at least one insight displayed at the user interface of the display device provides a second data element and/or property, the second data element and/or property being expected by the system. At least one aspect of the above example includes where the set of operations includes analyzing the portion of the digital healthcare record utilizing the second data element and/or property. At least one aspect of the above example includes where the one or more exceptions include an encoding of a received data value. At least one aspect of the above example includes where at least one insight displayed at the user interface of the display device provides a second encoding of the received data value, the second encoding being expected by the system. At least one aspect of the above example includes where the set of operations includes analyzing the portion of the digital healthcare record utilizing the second data encoding.

In accordance with at least one example of the present disclosure, a method is provided. The method may include receiving a portion of a digital healthcare record, analyzing the portion of the digital healthcare record for one or more exceptions, generating at least one insight based on the one or more exceptions, and causing the at least one insight to be displayed at a user interface of a display device.

At least one aspect of the above method may include where the one or more exceptions includes a received data value that is above or below a defined range. At least one aspect of the above method may include where the at least one insight displayed at the user interface of the display device provides a second data value based on the received data value that is out of range, the second data value being within the range. At least one aspect of the above method may include where the range is specific to a data type of the received data value. At least one aspect of the above method may include analyzing the portion of the digital healthcare record utilizing the second data value. At least one aspect of the above method may include receiving an indication to delay processing of the portion of the digital healthcare record. At least one aspect of the above method may include providing a proposed change to a processing rule associated with a data value included in the one or more exceptions. At least one aspect of the above method may include providing a proposed change to a processing rule associated with a data field included in the digital healthcare record. At least one aspect of the above method may include detecting an incorrectly identified data format, and mapping the incorrectly identified data format to a correct data format. At least one aspect of the above method may include where the one or more exceptions includes at least one unexpected received data element and/or an unexpected received object property. At least one aspect of the above method may include where the at least one insight displayed at the user interface of the display device provides a second data element and/or property, the second element and/or property being expected by the system. At least one aspect of the above method may include where the set of operations includes analyzing the portion of the digital healthcare record utilizing the second data element and/or property. At least one aspect of the above method may include where the one or more exceptions include an encoding of a received data value. At least one aspect of the above method may include where at least one insight displayed at the user interface of the display device provides a second encoding of the received data value, the second encoding being expected by the system. At least one aspect of the above method may include where the set of operations includes analyzing the portion of the digital healthcare record utilizing the second data encoding.

In accordance with at least one example of the present disclosure, a computer-readable medium including instructions that when executed by a processor, cause the processor to receive a portion of an digital healthcare record, analyze the portion of the digital healthcare record for one or more exceptions, generate at least one insight based on the one or more exceptions, and cause the at least one insight to be displayed at a user interface of a display device.

While illustrative examples of the disclosure have been described in detail herein, it is to be understood that the inventive concepts may be otherwise variously embodied and employed, and any appended claims are intended to be construed to include such variations, except as limited by the prior art.

What is claimed is:

1. A system comprising:
   at least one processor; and
   a non-transitory memory storing instructions that, when executed by the at least one processor, causes the system to perform a set of operations, the set of operations comprising:
   receiving a first healthcare record from a first source system;
   generating, by a first automated process, a first set of data items from the first healthcare record, the first automated process comprising natural language processing (NLP);
   comparing the first set of data items to a second set of data items of a template;
   detecting a missing data item which is absent from the first set of data items, based on the comparison with the template;
   determining that an exception exists based on the detection of the missing data item;
   generating an insight based on the exception;
   parking, in a deferral queue, queued data comprising one or more of the insight or the exception;
   comparing a number of exceptions to a threshold; and
   presenting, via a graphical user interface, an indication associated with the insight, the presentation based on the comparison to the threshold.

2. The system of claim 1, wherein the queued data comprises the exception and a plurality of further exceptions.

3. The system of claim 1, wherein the operations comprise:
   generating the missing data item based on the insight.

4. The system of claim 1, wherein the operations comprise:
   processing queued data from the deferral queue responsive to the number of exceptions of a document exceeding the threshold.

5. The system of claim 1, wherein the operations comprise:
   processing queued data from the deferral queue responsive to the number of exceptions of a healthcare record exceeding the threshold.

6. The system of claim 1, wherein generating the missing data item comprises:
   processing a non-discrete value to generate the missing data item.

7. The system of claim 1, wherein the insight comprises:
   generating a notification for conveyance to the graphical user interface indicative of the exception;
   receiving an update corresponding to the missing data item; and
   updating the first healthcare record.

8. The system of claim 1, wherein the operations comprise:
   receiving, from the graphical user interface, a selection of the indication; and
   generating a data item based on the receipt of the selection,
   wherein the indication is a suggestion associated with the insight.

9. A method, comprising:
   receiving, by one or more processors, a first healthcare record from a first source system;
   generating, by the one or more processors according to a first automated process, a first set of data items from the first healthcare record, the first automated process comprising natural language processing (NLP);
   comparing, by the one or more processors, the first set of data items to a second set of data items of a template;
   detecting, by the one or more processors, a missing data item which is absent from the first set of data items, based on the comparison with the template;
   determining, by the one or more processors, that an exception exists based on the detection of the missing data item;
   generating, by the one or more processors, an insight based on the exception;
   parking in a deferral queue, by the one or more processors, queued data comprising one or more of the insight or the exception;
   comparing, by the one or more processors, a number of exceptions to a threshold; and
   presenting, via a graphical user interface by the one or more processors, an indication associated with the insight, the presentation based on the comparison to the threshold.

10. The method of claim 9, wherein the queued data comprises the insight and a plurality of further insights.

11. The method of claim 9, comprising:
    generating, by the one or more processors, the missing data item based on the insight.

12. The method of to claim 9, comprising:
    processing, by the one or more processors, the queued data from the deferral queue responsive to the number of exceptions of a healthcare record exceeding the threshold.

13. The method of claim 9, wherein generating the missing data item comprises:
processing, by the one or more processors, a non-discrete value to generate the missing data item.

14. The method of claim 9, wherein the insight comprises:
generating, by the one or more processors, a notification for conveyance to the graphical user interface indicative of the exception;
receiving, by the one or more processors, an update corresponding to the missing data item; and
updating, by the one or more processors, the first healthcare record.

15. The method of claim 9, comprising:
receiving, by the one or more processors and from the graphical user interface, a selection of the indication; and
generating, by the one or more processors, a data item based on the receipt of the selection,
wherein the indication is a suggestion associated with the insight.

16. A system comprising one or more processors, the system configured to:
receive, by the one or more processors, a first healthcare record from a first source system;
generate, by a first automated process of the one or more processors, a first set of data items from the first healthcare record, the first automated process comprising natural language processing (NLP);
compare, by the one or more processors, the first set of data items to a second set of data items of a template;
detect, by the one or more processors, a missing data item which is absent from the first set of data items, based on the comparison with the template;
determine, by the one or more processors, an exception exists based on the detection of the missing data item;
generate, by the one or more processors, an insight based on the exception;
park, in a deferral queue by the one or more processors, queued data comprising one or more of the insight or the exception;
compare, by the one or more processors, a number of exceptions to a threshold; and
present, by the one or more processors via a graphical user interface, an indication associated with the insight, the presentation based on the comparison to the threshold.

17. The system of claim 16, comprising the one or more processors to:
process queued data from the deferral queue responsive to the number of exceptions of a document exceeding the threshold.

18. The system of claim 16, wherein the insight comprises:
generation of a notification for conveyance to the graphical user interface indicative of the exception;
receipt of an update corresponding to the missing data item; and
generation of an updated first healthcare record.

19. The system of claim 16, comprising the one or more processors to:
receive, from the graphical user interface, a selection of the indication; and
generate a data item based on the receipt of the selection,
wherein the indication is a suggestion associated with the insight.

20. The system of claim 16, comprising the one or more processors to:
process queued data from the deferral queue responsive to the number of exceptions of a healthcare record or a document exceeding the threshold.

* * * * *